United States Patent
Drummond et al.

(10) Patent No.: US 6,891,918 B2
(45) Date of Patent: May 10, 2005

(54) METHODS AND APPARATUS FOR ACQUIRING PERFUSION DATA

(75) Inventors: Danielle Drummond, Wauwatosa, WI (US); Kelly Lynn Karau, New Berlin, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 57 days.

(21) Appl. No.: 10/306,637

(22) Filed: Nov. 27, 2002

(65) Prior Publication Data

US 2004/0101090 A1 May 27, 2004

(51) Int. Cl.$^7$ .............................. A61B 6/00; H05G 1/60
(52) U.S. Cl. .............................. 378/5; 378/8; 378/98.9; 378/98.11; 600/425; 600/431
(58) Field of Search .............................. 378/4, 5, 8, 95, 378/98.9, 98.11; 600/407, 425, 431

(56) References Cited

U.S. PATENT DOCUMENTS

| | | | | |
|---|---|---|---|---|
| 4,029,963 A | * | 6/1977 | Alvarez et al. ................. 378/5 |
| 4,361,901 A | | 11/1982 | Daniels et al. |
| 4,445,226 A | * | 4/1984 | Brody ........................ 378/98.9 |
| 4,611,341 A | * | 9/1986 | Brody ....................... 378/98.11 |
| 4,626,688 A | * | 12/1986 | Barnes .................... 250/361 R |
| 4,662,379 A | * | 5/1987 | Macovski ................... 600/428 |
| 4,672,651 A | * | 6/1987 | Horiba et al. .................. 378/62 |
| 4,686,695 A | * | 8/1987 | Macovski ................... 378/146 |
| 4,736,398 A | * | 4/1988 | Graeff et al. ............... 378/98.3 |
| 4,963,746 A | * | 10/1990 | Morgan et al. ......... 250/363.02 |
| 5,115,394 A | * | 5/1992 | Walters ....................... 382/131 |
| 5,123,037 A | * | 6/1992 | Picard et al. ............... 378/98.2 |
| 5,247,559 A | * | 9/1993 | Ohtsuchi et al. ............... 378/53 |
| 5,253,282 A | * | 10/1993 | Pelc .......................... 378/98.2 |
| 5,459,769 A | * | 10/1995 | Brown .......................... 378/4 |
| 5,570,403 A | | 10/1996 | Yamazaki et al. |
| 5,661,774 A | * | 8/1997 | Gordon et al. .............. 378/101 |
| 5,665,971 A | | 9/1997 | Chen et al. |
| 6,018,562 A | | 1/2000 | Willson |
| 6,185,272 B1 | | 2/2001 | Hiraoglu et al. |
| 6,236,709 B1 | | 5/2001 | Perry et al. |
| 6,278,760 B1 | * | 8/2001 | Ogawa et al. .................. 378/5 |
| 6,285,740 B1 | * | 9/2001 | Seely et al. ................ 378/98.9 |
| 6,320,931 B1 | | 11/2001 | Arnold |
| 6,335,961 B1 | * | 1/2002 | Wofford et al. ............... 378/65 |
| 6,343,111 B1 | * | 1/2002 | Avinash et al. .......... 378/98.11 |
| 6,356,617 B1 | * | 3/2002 | Besch et al. ............. 378/98.11 |
| 6,366,635 B1 | * | 4/2002 | Op De Beek et al. .......... 378/4 |
| 6,369,389 B1 | | 4/2002 | Berlad et al. |
| 6,373,920 B1 | * | 4/2002 | Hsieh ....................... 378/98.11 |
| 6,397,097 B1 | * | 5/2002 | Requardt .................... 600/431 |
| 6,418,189 B1 | * | 7/2002 | Schafer ....................... 378/57 |
| 6,507,633 B1 | | 1/2003 | Elbakri et al. |
| 6,560,315 B1 | | 5/2003 | Price et al. |
| 2002/0163988 A1 | | 11/2002 | Nisius et al. |
| 2003/0063787 A1 | | 4/2003 | Natanzon et al. |
| 2004/0022359 A1 | * | 2/2004 | Acharya et al. ......... 378/98.11 |

\* cited by examiner

*Primary Examiner*—Allen C. Ho
(74) *Attorney, Agent, or Firm*—Armstrong Teasdale LLP

(57) ABSTRACT

A method for obtaining perfusion data includes providing an object of interest, estimating a first quantity of contrast agent utilized by a mono-energy computed tomography (CT) imaging system to image the object of interest, introducing a second quantity of contrast agent into the object of interest, the second quantity of contrast agent less than the first quantity of contrast agent, and scanning the object of interest using a multi-energy Computed Tomography (MECT) system to acquire data.

9 Claims, 4 Drawing Sheets

METHODS AND APPARATUS FOR ACQUIRING PERFUSION DATA

BACKGROUND OF THE INVENTION

This invention relates generally to medical imaging systems and more particularly to an apparatus and methods for discriminating multiple contrast agents using a medical imaging system.

In spite of recent advancements in computed tomography (CT) technology, such as faster scanning speeds, larger coverage with multiple detector rows, and thinner slices, energy resolution is still a missing piece. Namely, wide x-ray photon energy spectrum from the x-ray source and the lack of energy resolution from CT detection systems preclude energy discrimination CT.

X-ray attenuation through a given object is not a constant. Rather, the X-ray attenuation is strongly dependent on the x-ray photon energy. This physical phenomenon manifests itself in the image as beam-hardening artifacts, such as, non-uniformity, shading, and streaks. Some beam-hardening artifacts can be easily corrected, but other beam-hardening artifacts may be more difficult to correct. In general, known methods to correct beam hardening artifacts include water calibration, which includes calibrating each CT machine to remove beam hardening from materials similar to water, and iterative bone correction, wherein bones are separated in the first-pass image then correcting for beam hardening from the bones in the second-pass. However, beam hardening from materials other than water and bone, such as metals and contrast agents, may be difficult to correct. In addition, even with the above described correction methods, conventional CT does not provide quantitative image values. Rather, the same material at different locations often shows different CT numbers.

Another drawback of conventional CT is a lack of material characterization. For example, a highly attenuating material with a low density can result in the same CT number in the image as a less attenuating material with a high density. Thus, there is little or no information about the material composition of a scanned object is based solely on the CT number.

Additionally, assessment of the vasculature is often difficult since the images produced by such scanners may exhibit a significant level of image artifacts and CT number inaccuracy. These limitations may prevent the utilization of the CT device for advanced diagnosis. To improve the assessment of the vasculature, tissues, and organs, a relatively large dosage of contrast agent is administered to the patient to enhance image quality. It would therefore, be desirable to lower the dosage of contrast agent administered to the patient and/or correspondingly improve the image generated.

BRIEF DESCRIPTION OF THE INVENTION

In one aspect, a method for obtaining perfusion data is provided. The method includes providing an object of interest, estimating a first quantity of contrast agent utilized by a mono-energy computed tomography (CT) imaging system to image the object of interest, introducing a second quantity of contrast agent into the object of interest, the second quantity of contrast agent less than the first quantity of contrast agent, and scanning the object of interest using a multi-energy Computed Tomography (MECT) system to acquire data.

In another aspect, a method for obtaining perfusion data is provided. The method includes acquiring a first image of a contrast agent at a first energy during a first scan, acquiring a second image of a background tissue at a second energy during the first scan, and subtracting the second image from the first image to generate an enhanced image.

In another aspect, a multi-energy computed tomography (MECT) system is provided. The MECT includes at least one radiation source, at least one radiation detector, and a computer coupled to the radiation source and the radiation detector. The computer is configured to acquire a first image of a contrast agent at a first energy during a first scan, acquire a second image of a background tissue at a second energy during the first scan, and subtract the second image from the first image to generate an enhanced image.

In still another aspect, a computer readable medium encoded with a program is provided. The program is configured to instruct a computer to acquire a first image of a contrast agent at a first energy during a first scan, acquire a second image of a background tissue at a second energy during the first scan, and subtract the second image from the first image to generate an enhanced image.

In yet another aspect, a computer is provided. The computer is configured to acquire a first image of a contrast agent at a first energy during a first scan of a multi energy computed tomography (MECT) system, acquire a second image of a background tissue at a second energy during the first scan of the MECT, and subtract the second image from the first image to generate an enhanced image.

DETAILED DESCRIPTION OF THE INVENTION

Figure 1:
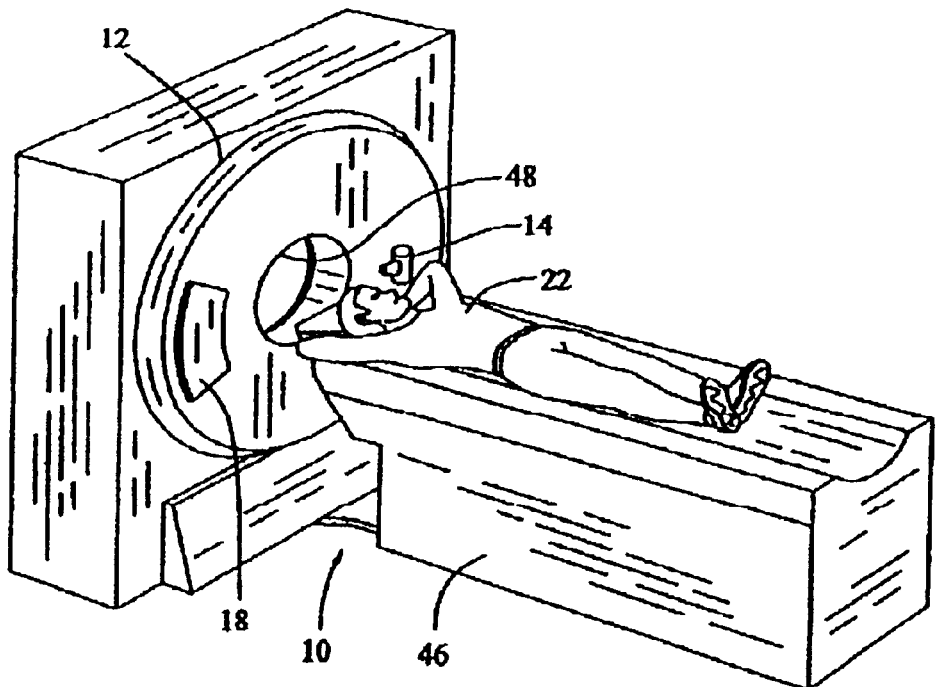
FIG. 1 is a pictorial view of a MECT imaging system.

The methods and apparatus described herein address acquiring perfusion data using an energy-discriminating (also known as multi-energy) computed tomography (MECT) system. To acquire perfusion data using at least one known system, an operator estimates a quantity of contrast agent to be used to generate an optimal image. Using the MECT system, the same operator can introduce less contrast agent into the patient and/or generate an improved image.

Additionally, the methods described herein include novel approaches to make use of the basic properties of the x-ray and material interaction. For example, for each ray trajectory, multiple measurements with different mean x-ray energies are acquired. When Compton and photoelectric decomposition and/or BMD are performed on these measurements, additional information is obtained that enables improved accuracy and characterization.

In some known CT imaging system configurations, an x-ray source projects a fan-shaped beam which is collimated to lie within an x-y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image. Additionally, scan, as used herein, describes performing multiple gantry rotations over a period of time. For example, in perfusion, approximately one hundred scans can be conducted over a single time interval, such as, but not limited to, approximately forty seconds.

Figure 2:
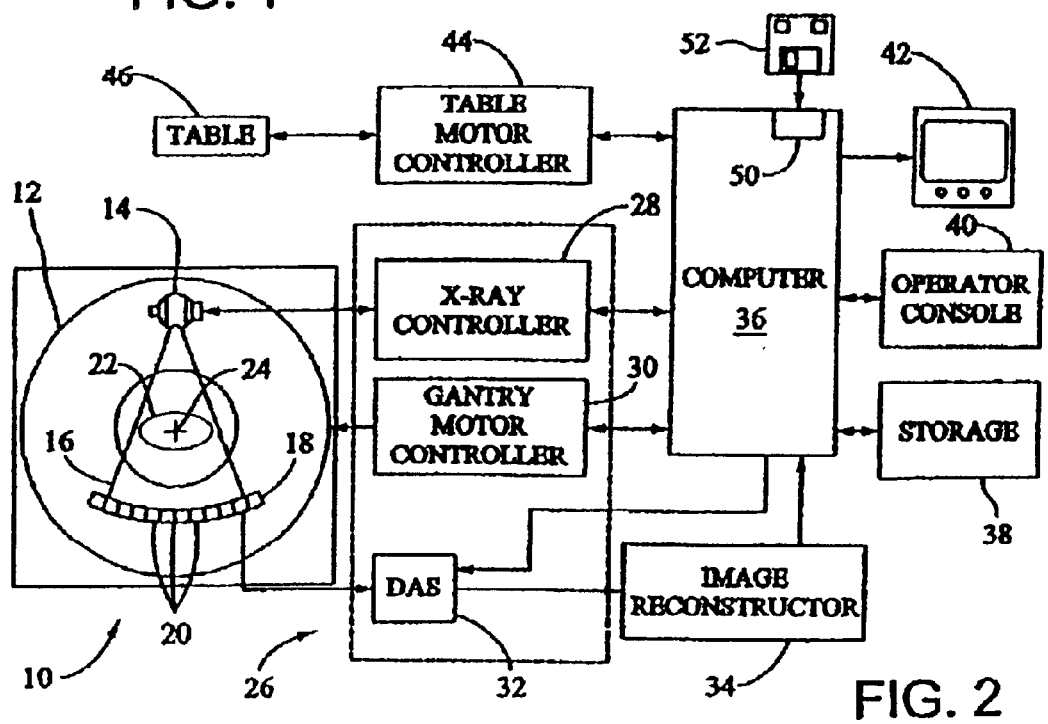
FIG. 2 is a block schematic diagram of the system illustrated in FIG. 1.

Referring to FIGS. 1 and 2, a multi-energy scanning imaging system, for example, a multi-energy multi-slice computed tomography (MECT) imaging system 10, is shown as including a gantry 12 representative of a "third generation" CT imaging system. As used herein, a multi-energy computed tomography system may also be referred to as an energy discrimination CT (EDCT) system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of MECT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD, a MOD or an other digital source such as a network or the Internet, as well as yet to be developed digital means. Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. CT imaging system 10 is an energy-discriminating (also known as multi-energy) computed tomography (MECT) system in that system 10 is configured to be responsive to different x-ray spectra. This can be accomplished with a conventional third generation CT system to acquire projections sequentially at different x-ray tube potentials. For example, two scans are acquired either back to back or interleaved in which the tube operates at 80 kVp and 160 kVp potentials, for example. Alternatively, special filters are placed between the x-ray source and the detector such that different detector rows collect projections of different x-ray energy spectrum. Alternatively, the special filters that shape the x-ray spectrum can be used for two scans that are acquired either back to back or interleaved. Yet another embodiment is to use energy sensitive detectors such that each x-ray photon reaching the detector is recorded with its photon energy. Although the specific embodiment mentioned above refers to a third generation CT system, the methods described herein equally apply to fourth generation CT systems (stationary detector—rotating x-ray source) and fifth generation CT systems (stationary detector and x-ray source).

There are different methods to obtain multi-energy measurements: (1) scan with two distinctive energy spectra, (2) detect photon energy according to energy deposition in the detector, and (3) photon counting. Photon counting provides clean spectra separation and an adjustable energy separation point for balancing photon statistics.

MECT facilitates reducing or eliminating a plurality of problems associated with conventional CT, such as, but not limited to, a lack of energy discrimination and material characterization. In the absence of object scatter, system 10 can be used to separately detect two regions of photon energy spectrum: the low-energy and the high-energy portions of the incident x-ray spectrum. The behavior at any other energy can be derived based on the signal from the two energy regions. This phenomenon is driven by the fundamental fact that in the energy region where medical CT is interested, two physical processes dominate the x-ray attenuation: (1) Compton scatter and the (2) photoelectric effect. Thus, detected signals from two energy regions provide sufficient information to resolve the energy dependence of the material being imaged. Furthermore, detected signals from two energy regions provide sufficient information to determine the relative composition of an object composed of two materials.

In an exemplary embodiment, MECT uses a decomposition algorithm, such as, but not limited to, a CT number difference algorithm, a Compton and photoelectric decomposition algorithm, a basis material decomposition (BMD) algorithm, and a logarithm subtraction decomposition (LSD) algorithm.

The CT number difference algorithm includes calculating a difference value in a CT or a Hounsfield number between two images obtained at different tube potentials. In one embodiment, the difference values are calculated on a pixel-by-pixel basis. In another embodiment, average CT number differences are calculated over a region of interest. The Compton and photoelectric decomposition algorithm includes acquiring a pair of images using MECT 10, and separately representing the attenuations from Compton and photoelectric processes. The BMD algorithm includes acquiring two CT images; wherein each image represents the equivalent density of one of the basis materials. Since a material density is independent of x-ray photon energy, these images are approximately free of beam-hardening artifacts. Additionally, an operator can choose the basis material to target a certain material of interest, thus enhancing the image contrast. In use, the BMD algorithm is based on the concept that the x-ray attenuation (in the energy region for medical CT) of any given material can be represented by proper density mix of other two given materials, accordingly, these two materials are called the basis materials. In one embodiment, using the LSD algorithm, the images are acquired with quasi-monoenergetic x-ray spectra, and the imaged object can be characterized by an effective attenuation coefficient for each of the two materials, therefore the LSD algorithm does not incorporate beam-hardening corrections. Additionally, the LSD algorithm is not calibrated, but uses a determination of the tissue cancellation parameters, which are the ratio of the effective attenuation coefficient of a given material at the average energy of each exposure. In an exemplary embodiment, the tissue cancellation parameter is primarily dependent upon the spectra used to acquire the images, and on any additional factors that change the measured signal intensity from that which would be expected for a pair of ideal, mono-energetic exposures.

It should be noted that in order to optimize a multi-energy CT system, the larger the spectra separation, the better the image quality. Also, the photon statistics in these two energy regions should be similar, otherwise, the poorer statistical region will dominate the image noise.

Figure 3:
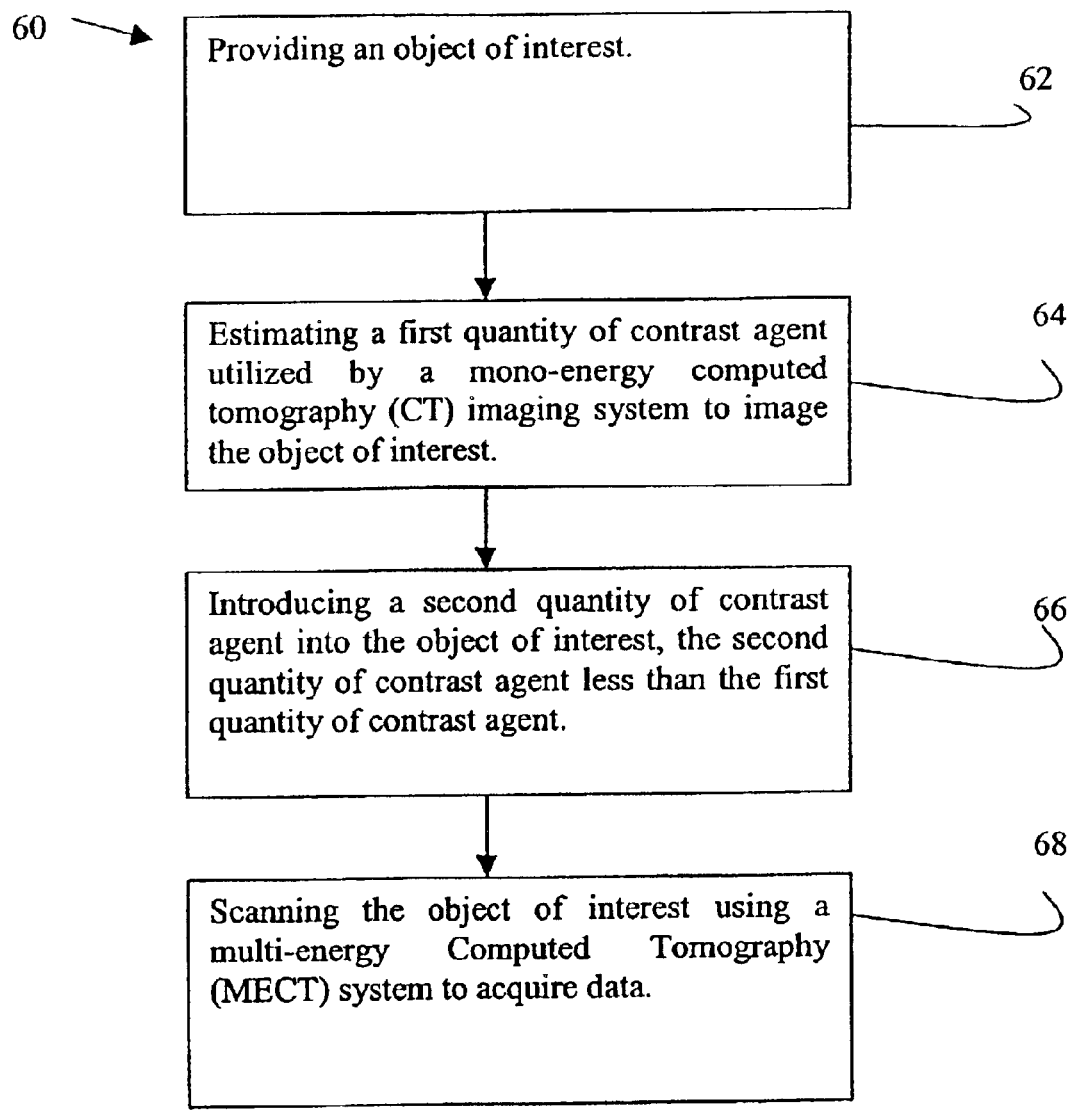
FIG. 3 is a method for obtaining perfusion data.

FIG. 3 is a method 60 for obtaining perfusion data using the medical imaging system illustrated in FIG. 1. Method 60 includes providing 62 an object of interest, such as patient 22, estimating 64 a first quantity of contrast agent utilized by a mono-energy computed tomography (CT) imaging system to image the object of interest, introducing 66 a second quantity of contrast agent into the object of interest, the second quantity of contrast agent less than the first quantity of contrast agent, and scanning 68 the object of interest using a multi-energy Computed Tomography (MECT) system to acquire data. As used herein, mono-energy computed tomography refers to system that acquire data relating to a single x-ray spectrum during a single data acquisition, while MECT refers to systems that acquire data relating to two or more x-ray spectra during a single data acquisition.

In use, a catheter or other appropriate medical device, is inserted into an arterial vessel upstream of the tissue or organ that is selected to be imaged. A contrast agent is then injected into the artery using the catheter. In an exemplary embodiment, the quantity of contrast agent used is determined by the operator based on known mono-energetic CT imaging techniques. Using the MECT, the quantity of contrast agent injected in the patient is reduced. In one embodiment, the quantity of contrast agent used in a MECT procedure is reduced at least approximately 25% from that used when imaging utilizing at least one known CT imaging system. In another embodiment, the contrast agent is reduced between approximately 10% and approximately 60%. In another embodiment, the contrast agent is reduced between approximately 25% and approximately 75%. In one embodiment, the contrast agent includes, but is not limited, to a chelate of gadolinium such as Gd-DTPA, a non-ionic chelate such as gadodiamide (gadolinium-diethylenetriamine penta-acetic acid bismethylamide, $C_{16}H_{28}GdN_5O_9xH_2O$), or an ionic or non-ionic iodine-based agent such as Iopamidol.

Scanning 68 the object of interest using a multi-energy Computed Tomography (MBCT) system to acquire data also includes generating a first image of a contrast agent at a first energy during a first scan and generating a second image of a background tissue at a second energy during the first scan. The second image is then subtracted from the first image to generate a final image of the contrast agent at an increased signal level.

In use, the final image can be processed using known principles, such as, but not limited to the Fick Principle:

$$Q(T) = BF \cdot \int_0^T C_a(t)\,dt \qquad \text{Equation 1}$$

$$BF = \frac{Q(T)}{\int_0^T C_a(t)\,dt} \qquad \text{Equation 2}$$

where:
Q(T) is a tissue enhancement curve;
BF is a blood flow; and
$C_a(t)$ is a contrast agent perfusion over time.

In an exemplary embodiment, BF is for example a cerebral blood flow (CBF). As shown in Equation 1 and Equation 2, $C_a(t)$ and Q(T) are contrast agent attenuation over a series of images. For example, Q(T) is over an area of tissue. $C_a(t)$ is measured in a feeding artery, and also represents an "arterial concentration curve" described herein. In use, the methods described herein facilitate modeling $C_a(t)$ to approximate a delta function, i.e. an integral of which is 1, such that the denominator in equation 2 is approximately equal to 1. Modeling $C_a(t)$ to approximate a delta function provides an improved approximation of the contrast agent attenuation through the tissue over the time series of images.

Figure 4:
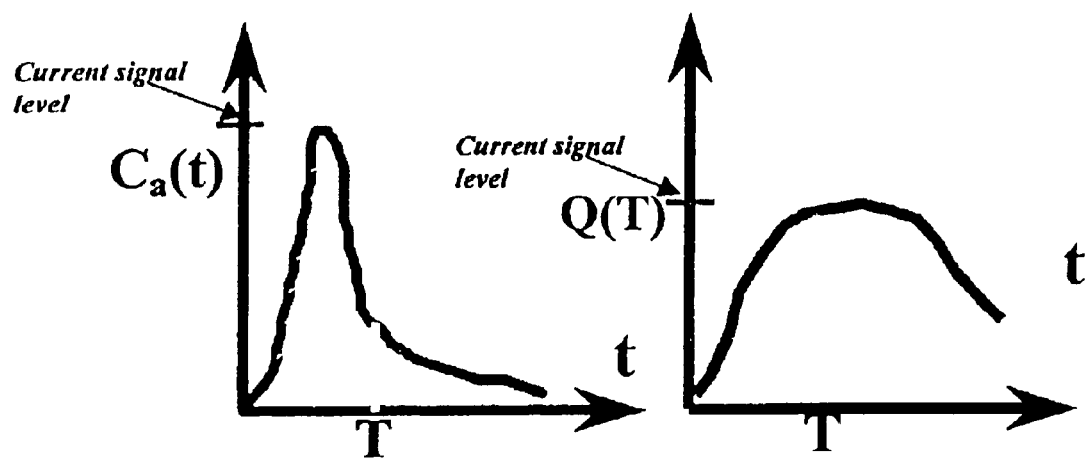
FIG. 4 illustrates an enhancement signal acquired using a mono-energy CT imaging system when a first quantity of contrast agent has been introduced into a patient.
Figure 5:
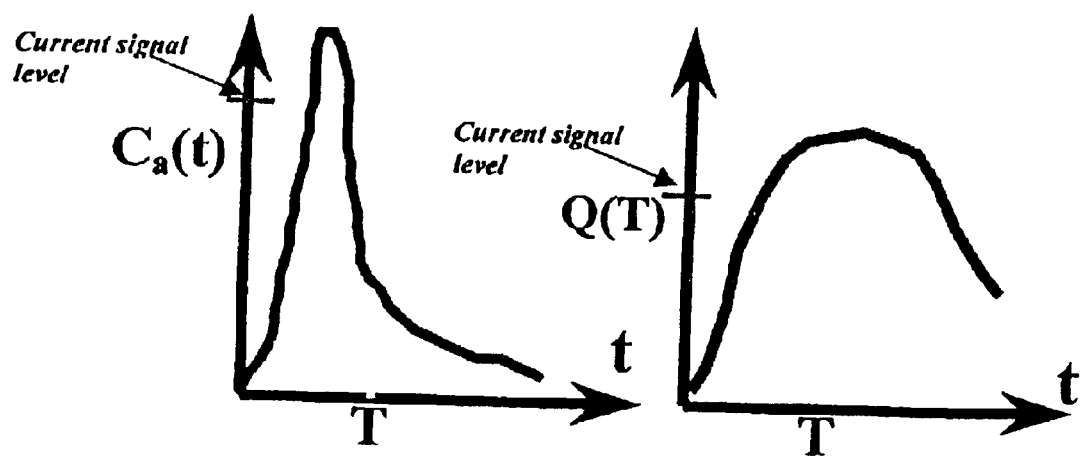
FIG. 5 illustrates an enhancement signal acquired using the MECT system shown in FIG. 1 when the first quantity of contrast agent has been introduced into the patient.

FIG. 4 is a an enhancement signal acquired using a mono-energy CT imaging system when a first quantity of contrast agent has been introduced into patient 22. FIG. 5 is an enhancement signal acquired using MECT system 10 when the first quantity of contrast agent has been introduced into patient 22. As shown in FIG. 5, the current signal levels are greater than the signal levels shown in FIG. 4.

As shown in FIG. 5, using MECT system 10 facilitates differentiating the contrast agent from the background tissue and provides an enhanced contrast signal. As a result, the arterial concentration curve more closely resembles an impulse function, thus improving the accuracy of the resulting flow function, CBF in the case of brain perfusion, or other flow signals in independent perfusion applications.

Figure 6:
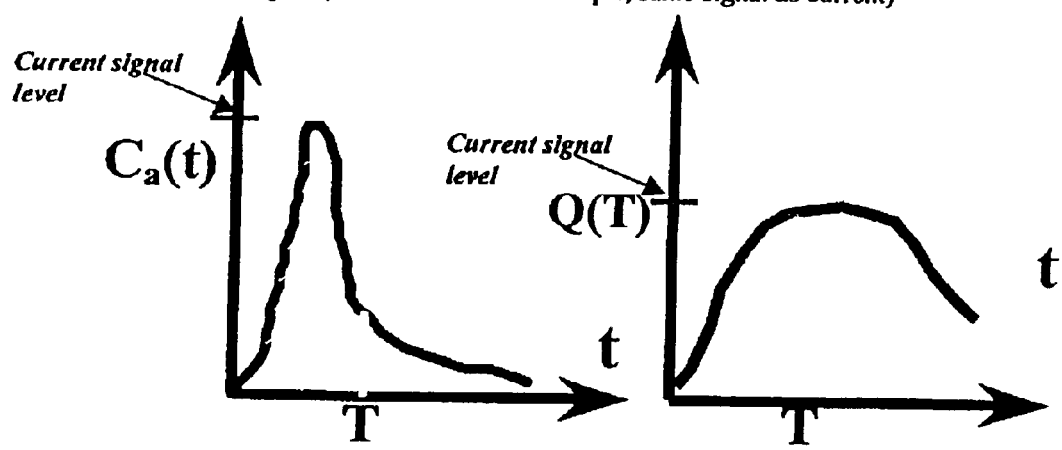
FIG. 6 illustrates an enhancement signal acquired using the MECT system shown in FIG. 1 using a second quantity of contrast agent, less than the first quantity of contrast agent.

FIG. 6 is an enhancement signal acquired using MECT system 10 using a second quantity of contrast agent, less than the first quantity of contrast agent. In use, the methods described herein improve the signal to noise ratio in the perfusion images, resulting in more accurate quantification of functional parameters. Therefore, a reduced level of contrast agent can be administered to patient 22 for a given perfusion study. In conjunction with the reduced contrast dose, multiple location imaging can also be accomplished, thus allowing greater anatomical coverage. Finally, the improvement of beam hardening artifact as related to contrast agents allows for more formidable, new applications in myocardial perfusion which are currently limited by beam hardening due to excessive contrast in the ventricles of the heart.

While the invention has been described in terms of various specific embodiments, those skilled in the art will recognize that the invention can be practiced with modification within the spirit and scope of the claims.

What is claimed is:

1. A method for obtaining perfusion data, said method comprising:

providing an object of interest;

estimating a first quantity of contrast agent utilized by a mono-energy computed tomography (CT) imaging system to image the object of interest;

introducing a second quantity of contrast agent into the object of interest, the second quantity of contrast agent less than the first quantity of contrast agent; and scanning the object of interest using a multi-energy Computed Tomography (MECT) system to acquire data.

2. A method in accordance with claim 1 further comprising:

acquiring a first image of a contrast agent at a first energy during a first scan;

acquiring a second image of a background tissue at a second energy during the first scan; and subtracting the second image from the first image to generate an enhanced image.

3. A method in accordance with claim 1 wherein said introducing a second quantity of contrast agent comprises introducing a second quantity of contrast agent into the object of interest, the second quantity of contrast agent less than the first quantity of contrast agent by at least 10%.

4. A method in accordance with claim 1 wherein said introducing a second quantity of contrast agent comprises introducing a second quantity of contrast agent into the object of interest, the second quantity of contrast agent less than the first quantity of contrast agent by at least 25%.

5. A method in accordance with claim 4 wherein said introducing a second quantity of contrast agent comprises introducing a second quantity of contrast agent into the object of interest, the second quantity of contrast agent less than the first quantity of contrast agent by at most 60%.

6. A method in accordance with claim 4 wherein said introducing a second quantity of contrast agent comprises introducing a second quantity of contrast agent into the object of interest, the second quantity of contrast agent less than the first quantity of contrast agent by at most 75%.

7. A multi-energy computed tomography (MECT) system comprising:

at least one radiation source;

at least one radiation detector; and a computer coupled to said radiation source and said radiation detector, said computer configured to:

introduce a quantity of contrast into a first vessel wherein the quantity of contrast is less than a quantity utilized by a mono-energy computed tomography (CT);

acquire a first image of the contrast agent at a first energy during a first scan;

acquire a second image of a background tissue at a second energy during the first scan;

decompose the first and second images using at least one of a CT number difference algorithm and a basis material decomposition (BMD) algorithm; and subtract the second image from the first image to generate an enhanced image.

8. A computer readable medium encoded with a program configured to instruct a computer to:

introduce a quantity of contrast agent into a first vessel wherein the quantity of contrast agent is less than a quantity utilized by a mono-energy computed tomography (CT);

acquire a first image of the contrast agent at a first energy during a first scan;

acquire a second image of a background tissue at a second energy during the first scan;

decompose the first and second images using at least one of a CT number difference algorithm and a basis material decomposition (BMD) algorithm; and subtract the second image from the first image to generate an enhanced image.

9. A computer configured to:

introduce a quantity of contrast into a first vessel wherein the quantity of contrast is less than a quantity utilized by a mono-energy computed tomography (CT);

acquire a first image of a contrast agent at a first energy during a first scan of the multi-energy computed tomography (MECT) system;

acquire a second image of a background tissue at a second energy during the first scan of the MECT;

decompose a plurality of projections relating to said first and second images prior to generating the first and second images by using at least one of a CT number difference algorithm and a basis material decomposition (BMD) algorithm; and subtract the second image from the first image to generate an enhanced image.

* * * * *